United States Patent [19]

Biziere et al.

[11] Patent Number: 4,540,696
[45] Date of Patent: Sep. 10, 1985

[54] 1-PIPERAZINYL 4-PHENYLQUINAZOLINE COMPOUNDS HAVING ANTIDEPRESSANT PROPERTIES AND DRUGS CONTAINING SAME

[75] Inventors: Kathleen Biziere, Clapiers; André Hallot, Saint-Gely-du-Fesc; Jean-Paul Kan, Clapiers, all of France

[73] Assignee: Sanofi S.A., France

[21] Appl. No.: 463,386

[22] Filed: Feb. 3, 1983

[30] Foreign Application Priority Data

Feb. 8, 1982 [FR] France .................. 82 01988

[51] Int. Cl.³ .................. A61K 31/505; C07D 403/04
[52] U.S. Cl. .................. 514/254; 544/283; 544/286; 544/292
[58] Field of Search .................. 544/292; 424/251

[56] References Cited

U.S. PATENT DOCUMENTS

| | | | |
|---|---|---|---|
| 3,305,553 | 2/1967 | Hoefle et al. | 544/292 |
| 3,509,141 | 4/1970 | Walker | 424/251 |
| 3,511,836 | 5/1970 | Hess | 544/292 |
| 3,635,979 | 1/1972 | Hess | 544/292 |
| 3,646,028 | 2/1972 | Walker | 544/292 |
| 4,499,042 | 2/1985 | Hallot et al. | 544/292 |

FOREIGN PATENT DOCUMENTS

| | | | |
|---|---|---|---|
| 0087337 | 8/1983 | European Pat. Off. | 544/292 |
| 2514765 | 4/1983 | France | 544/292 |
| 56-92875 | 7/1981 | Japan | 544/292 |

OTHER PUBLICATIONS

Saleta et al., "Chemical Abstracts", vol. 89, 1978, Col. 89:43492s.

Primary Examiner—Glennon H. Hollrah
Assistant Examiner—James H. Turnipseed
Attorney, Agent, or Firm—Ostrolenk, Faber, Gerb & Soffen

[57] ABSTRACT

The present invention relates to new derivatives of formula:

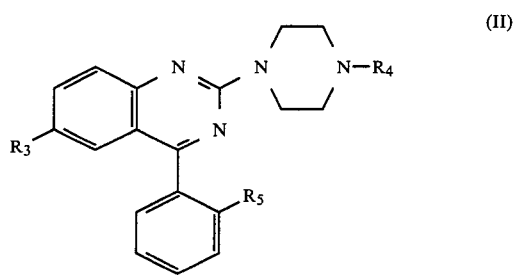

in which:
R₃ denotes a halogen, preferably chlorine, or a nitro group,
R₄ represents hydrogen or a lower alkyl group having from 1 to 4 atoms of carbon,
R₅ represents an atom of halogen, preferably chlorine or fluorine.

It also relates to a process for preparing products of formula (II) and to the drugs containing at least one product of formula (II).

16 Claims, No Drawings

1-PIPERAZINYL 4-PHENYLQUINAZOLINE COMPOUNDS HAVING ANTIDEPRESSANT PROPERTIES AND DRUGS CONTAINING SAME

The present invention relates to new derivatives of 4-piperazinyl 4-phenyl quinazoline having antidepressant properties, to a process for preparing said compounds and to drugs containing same.

In an earlier Application (French Patent Application No. 81 19767), Applicants described derivatives of 4-phenyl quinazoline corresponding to general formula:

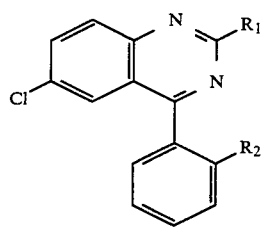

in which $R_1$ denotes a tertiary amine group, cyclic or not, itself bearing a hydroxyl group, and $R_2$ represents an atom of chlorine or of fluorine.

Compounds (I) are endowed with antiepileptic and narcosis potentialization properties allowing them to be used as drugs by way of minor tranquillizers, hypnotics and antiepileptics.

It has been unexpectedly found that, by varying the nature of substituent $R_1$, the products obtained no longer present the pharmacological properties of products (I), but are endowed with highly interesting antidepressant properties.

According to the invention, the new compounds correspond to general formula:

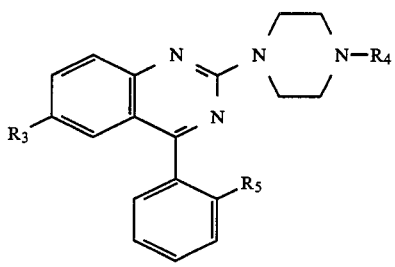

in which:

$R_3$ denotes a halogen, preferably chlorine, or a nitro group, $R_4$ represents hydrogen or a lower alkyl group having from 1 to 4 atoms of carbon, $R_5$ represents an atom of halogen, preferably chlorine or fluorine.

Compounds (II) furnish soluble salts with the mineral or organic acids. These salts, with pharmaceutically acceptable acids, form part of the invention.

Compounds (II) may be prepared from a 4-phenyl 2-quinazoline suitably substituted (I) according to the reaction diagram:

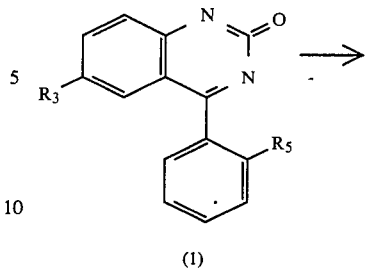

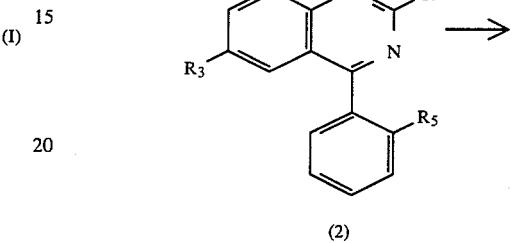

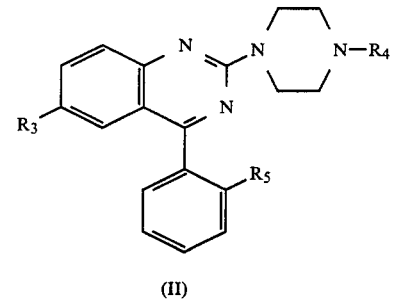

By action on the quinazolone (I) of a chlorinated derivative of phosphorus, the derivative (2) chlorinated in 2 position is obtained. Phosphorus oxychloride is most often used. Operation may be carried out within an inert solvent such as an aromatic hydrocarbon (benzene or toluene) but, most often, it is preferred to use an excess of oxychloride as solvent. The reaction takes place at a temperature of between 60° and 120° C. and, most often, at the boiling temperature of the solvent used.

Corresponding compound (II) is obtained from the chlorinated derivative (2), by action of an amine

in excess within an inert solvent such as ethanol. Operation is generally carried out by heating to the boiling temperature of the solvent.

The salts of compounds (II) are conventionally obtained by salifying the base, hot, by a stoichiometric quantity of acid within a suitably chosen solvent so that the salt formed crystallizes by cooling.

The starting quinazolones (1) are known compounds. When $R_3$=halogen, they may in particular be prepared by action of potassium cyanate on a suitably substituted 2-amine 5-halogen benzophenone.

When $R_3$ represents the nitro group, compounds (1) may be obtained by action of the urea on a suitably substituted 2-amino 5-nitro benzophenone.

The following examples are given by way of illustration for the preparation of the compounds (II) according to the method indicated hereinbefore.

EXAMPLE 1

2-(1-methyl 4-piperazinyl) 4-(2-chloro phenyl) 6-nitro quinazoline (CM 40498)

(II) $R_3=NO_2$; $R_4=CH_3$; $R_5=Cl$ (a) 2-chloro 4-(2-chloro phenyl) 6-nitro quinazoline A mixture of 40 g of 4-(2-chloro phenyl) 6-nitro 2-quinazolone are 600 ml of phosphorus oxychloride is heated to reflux for 4 hours. The phosphorus oxychloride is evaporated in vacuo to dryness, then the residue is poured into an ice-water mixture. It is rendered alkaline with a 10% sodium hydroxide solution. The precipitate is drained and washed with acetonitrile. The product is purified by chromatography over a column of silica. By eluting with a chloroform-methanol (95-5 vol/vol) mixture, the expected product is isolated. Weight: 27 g; m.p.: 228° C. (isopropanol).

(b) CM 40498

A mixture of 3.2 g of the chlorinated derivative obtained hereinabove and 3 g of N-methyl piperazine in 120 ml of absolute ethanol is heated to reflux for 3 hours. The solvent is evaporated to dryness in vacuo, then the residue is taken up in ethyl acetate. The solution is washed with an aqueous solution of sodium carbonate and then with water. The solution is dried over sodium sulfate and then evaporated to dryness. The residue is recrystallized in a methanol-dichloromethane mixture. Crystals are obtained. Weight: 3.1 g; m.p.: 204° C.

EXAMPLES 2 to 6

(a) By operating as in Example 1a), but by varying the quinazolone, the following are obtained in the same manner:

2-chloro 4-(2-fluoro phenyl) 6-nitro quinazoline; m.p.: higher than 260° C. (isopropanol)

2,6-dichloro 4-(2-chloro phenyl) quinazoline m.p.: 175°–176° C. (ethanol)

2,6-dichloro 4-(2-fluoro phenyl) quinazoline m.p.: 208°–210° C. (acetonitrile)

(b) From the various derivatives chlorinated in 2 position mentioned hereinbefore and by varying the

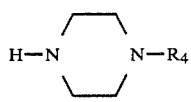

amine used, the different compounds (II) shown in Table I hereinafter are obtained as indicated in Example 1b).

The products according to the invention have been subjected to pharmacological trials with a view to determining their activity on the central nervous system. The various tests to which the products have been subjected will be indicated hereinbelow. In all cases, the products under study were administered per os.

A—PORSOLT TEST

This test was carried out in the female mouse, CDI (Charles Rivers, France) weighing from 18 to 23 g, according to the method described by Porsolt (Archives Internationales de Pharmacologie, 1977, 229, 327–336).

The principle of this test is as follows: when a mouse is placed in a narrow recipient, filled with water, it struggles and then, after 2 to 4 minutes, becomes still and floats on its stomach, its back rounded and its rear paws brought underneath its body; it makes only the few movements to enable it to hold its head out of the water. This is the so-called despair reaction.

Certain psychotherapeutics, particularly antidepressants, lengthen the time during which the mouse struggles.

The following protocol was chosen:

The products to be studied were administered orally to batches of 10 mice. 1 hour later, the animals are placed in a narrow receipient (10×10×10 cm), filled with water up to a height of 6 cm, the temperature of the water being 24° C. The animals are left in the water for 6 minutes and the time during which the animal remains immobile between the second and the sixth minute is measured—the shorter the time, the more the substance is active.

The results are expressed as the reduction in the immobilization time with respect to controls.

B—ANTAGONISM OF PTOSIS INDUCED BY RESERPINE

The majority of antidepressants antagonize the ptosis induced by reserpine. This test described by Gouret [Journal de Pharmacologie (Paris), 1973, 4(1), 105–128] was made in the female mouse, CDI (Charles Rivers, France) weighing from 18 to 23 g. The reserpine causes a ptosis 1 hour after its intravenous administration; certain antidepressants, particularly the imipraminics, oppose this ptosis.

The following protocol has been chosen:

The substances to be studied were administered per os to batches of 10 mice. The reserpine was administered simultaneously by the intravenous route at the dose of 2 mg/kg. 1 hour after the administration of reserpine, the number of animals not presenting ptosis is noted.

C—ANTAGONISM OF THE HYPOTHERMIA INDUCED BY RESERPINE

The majority of antidepressants antagonize the hypothermia induced by reserpine. This test was carried out according to the method described by HINO et Coll [Chem Pharm Bull 28 (9), 2618–2622, 1980] on female mice, CDI (Charles Rivers, France) weighing from 18 to 23 g.

The following protocol was chosen:

The substances to be studied are administered per os to batches of 10 mice, the controls receive the solvent along, simultaneously, the reserpine is administered i.p. at the dose of 5 mg/kg. The temperature of each animal is taken immediately before administration of the products to be tested and 4 hours afterwards. For each animal, the difference in temperature before and after treatment is calculated. The results are expressed in percentage of antagonism of the hypothermia observed in the controls.

D—POTENTIALIZATION OF THE TOXICITY OF YOHIMBINE

The majority of antidepressants potentialize the toxicity of yohimbine. This test was carried out according to the method described by MALICK (in Antidepressants: Neurochemical Behavioural and Clinical Perspectives, eds S. J. Enna, J. B. Malick, E. Richelson, Raven Press, New York, pages 141–153) on female mice, CDI (Charles Rivers, France).

The substances to be studied are administered per os to batches of 10 mice. The yohimbine is administered i.p. 1 hour later at the dose of 30 mg/kg. Mortality is noted 18 hours later.

E—ANTAGONISM OF THE TREMORS INDUCED BY OXOTREMORINE

The cholinergic effects of the imipramine are considered as being responsible for certain undesirable secondary effects of this substance. These effects are demonstrated by the antagonism of the tremors induced by oxotremorine. This test was carried out on female mice, CDI (Charles Rivers, France) weighing from 18 to 23 g. The following protocol was chosen:

The products to be studied are administered at time 0 by the oral route to batches of 10 mice. At time 60 mins., the oxotremorine is administered per os at the dose of 1 mg/kg. The number of mice which do not tremble 30 mins. after the administration of oxotremorine is noted.

All the pharmacological results obtained with various compounds according to the invention are set forth in Table II hereinafter. This Table also shows the results obtained, on the one hand, with imipramine, which is a compound whose antidepressant properties are widely used in therapeutics and, on the other hand, with compound CM 40331 or hydrochloride of 6-chloro 4-(2-chloro phenyl) 2-(4-hydroxy 1-piperidinyl) quinazoline, the compound described by Applicants in its French Patent Application No. 81 19767.

The results of Table II clearly show that the products according to the invention possess a powerful antidepressant activity. This activity is, in the majority of cases, more powerful than that of imipramine and is accompanied by a toxicity and secondary effects of cholinergic type clearly less than those of imipramine.

Furthermore, it may be noted that the product CM 40331 studied in comparison is virtually inactive on the tests carried out.

Consequently, the products according to the invention may be used in human therapeutics for the treatment of neuropsychic disorders such an endogenous, reactional or neurotic depressive states as well as for the treatment of depression in senile involution.

The products may be presented in the galenic forms corresponding to the oral route (tablets, capsules, etc . . . ) and to the parenteral route (injectable ampoules).

Dosage, which varies as a function of the disorders to be treated and of the mode of administration, will be progressive and will be between 50 and 300 mg per day in the adult.

By way of example, the following galenic preparation containing a product of the invention may be indicated:

| CAPSULE | |
|---|---|
| CM 40468 | 0.025 g |
| Starch STA RX 1500 | 0.140 g |
| Aerosil 200 | 0,0005 g |
| Magnesium stearate | 0.0015 g |
| for a No. 3 capsule | |

TABLE I

| Example n° | Code No. of product | $R_3$ | $R_4$ | $R_5$ | Base or salt Melting point (solvent) |
|---|---|---|---|---|---|
| 2 | 40460 | Cl | $CH_3$ | Cl | Hydrochloride m.p. > 260° C. (methanol) |
| 3 | 40468 | Cl | $CH_3$ | F | Base m.p.: 146–148° C. (methanol) |
| 4 | 40508 | $NO_2$ | $CH_3$ | F | Base m.p.: 220–222° C. (ethanol) |
| 5 | 41125 | Cl | H | F | Hydrochloride m.p. > 260° C. (isopropanol) |
| 6 | 41128 | Cl | $-CH_2CH_2CH_3$ | F | Base 130–132° C. (ethanol) |

TABLE II

| Products n° | Toxicity | Porsolt test (dose in mg/kg) | Antagonism of ptosis induced by reserpine ED 50 (mg/kg) | Antagonism of hypothermia induced by reserpine (at 10 mg/kg) | Potentialization of yohimbine ED 50 (mg/kg) | Antagonism of oxotremorine ED 50 (mg/kg) |
|---|---|---|---|---|---|---|
| 40 498 | Atoxic at 1 g/kg | −31%** (10) | 2.8 | +68%** | 7.8 | 43.5 |
| 40 460 | LD 80 = 1 g/kg | −11%* (10) | 2.1 | +71%** (at 20 mg/kg) | 5.4 | 142 |
| 40 468 | Atoxic at 1 g/kg | −61%** (10) | 0.98 | +73%** | 1.65 | 50 |
| 41 125 | LD 40 = 1 g/kg | −46** (5) | 0.48 | +81%** | 0.74 | 9.5 |
| 41 128 | Atoxic at 1 g/kg | −31** (5) | 6.2 | +62%** | 1.7 | — |
| Imipramine | LD 50 = 453 mg/kg | −30%** (10) | 2.4 | +59%** | 9.1 | 12 |
| 40 331 | Atoxic at 500 mg/kg | — | 0% at 100 mg/kg | −20% at 100 mg/kg | 10% at 100 mg/kg | — |

**p < 0.01

What is claimed is:

1. 4-piperazinyl 4-phenyl quinazoline compounds of the formula:

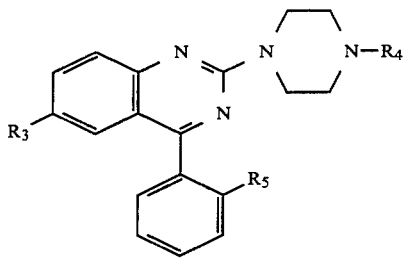

(II)

in which:
R$_3$ denotes a halogen or a nitro group,
R$_4$ represents H or an alkyl group having from 1 to 4 atoms of carbon,
R$_5$ represents a halogen and the salts of said derivatives with acids.

2. The compound of claim 1 wherein R$_5$ is chlorine or fluorine.
3. The compound of claim 2 wherein R$_3$ is nitro.
4. The compound of claim 3 wherein R$_4$ is methyl.
5. The compound of claim 2 wherein R$_3$ is chlorine.
6. The compound of claim 5 wherein R$_4$ is hydrogen, methyl or propyl.
7. The compound of claim 1 wherein R$_3$ is nitro, R$_4$ is methyl and R$_5$ is chlorine.
8. A pharmaceutical composition comprising an antidepressant effective amount of a compound according to claim 1 and a pharmaceutically acceptable carrier therefor.
9. The pharmaceutical composition of claim 8 wherein R$_3$ is chlorine or nitro and R$_5$ is chlorine or fluorine.
10. The pharmaceutical composition of claim 9 wherein R$_4$ is hydrogen, methyl or propyl.
11. The pharmaceutical composition of claim 10 wherein R$_3$ is nitro, R$_4$ is methyl and R$_5$ is chlorine.
12. The pharmaceutical composition of claim 11 wherein said carrier is an oral or parental administration carrier.
13. A method which comprises administering an antidepressant effective amount of a compound according to claim 1 to a host in need thereof.
14. The method of claim 13 wherein R$_3$ is chlorine or nitro and R$_4$ is chlorine or fluorine.
15. The method of claim 14 wherein R$_4$ is hydrogen, methyl or propyl.
16. The method of claim 15 wherein R$_3$ is nitro, R$_4$ is methyl and R$_5$ is chlorine.

* * * * *